(12) United States Patent
Panzera et al.

(10) Patent No.: US 7,011,522 B2
(45) Date of Patent: Mar. 14, 2006

(54) METHODS OF PRODUCING DENTAL RESTORATIONS USING CAD/CAM AND MANUFACTURES THEREOF

(75) Inventors: Carlino Panzera, Hillsborough, NJ (US); Dmitri Brodkin, West Orange, NJ (US); Paul Panzera, Mt. Holly, NJ (US)

(73) Assignee: Pentron Ceramics, Inc., Somerset, NJ (US)

( * ) Notice: Subject to any disclaimer, the term of this patent is extended or adjusted under 35 U.S.C. 154(b) by 283 days.

(21) Appl. No.: 10/027,017

(22) Filed: Dec. 18, 2001

(65) Prior Publication Data
US 2002/0155412 A1    Oct. 24, 2002

Related U.S. Application Data

(62) Division of application No. 09/376,921, filed on Aug. 18, 1999, now Pat. No. 6,354,836.

(60) Provisional application No. 60/097,216, filed on Aug. 20, 1998.

(51) Int. Cl.
A61C 13/00    (2006.01)
(52) U.S. Cl. ........................................ 433/215; 433/223
(58) Field of Classification Search ................ 433/215, 433/223, 202.1, 218
See application file for complete search history.

(56) References Cited

U.S. PATENT DOCUMENTS

| 4,187,608 | A | * | 2/1980 | Nyce ........................ 433/201.1 |
| 4,265,669 | A | * | 5/1981 | Starling et al. ............. 501/153 |
| 4,663,720 | A | | 5/1987 | Duret |
| 4,798,536 | A | | 1/1989 | Katz |
| 4,954,080 | A | * | 9/1990 | Kelly et al. ..................... 433/8 |
| 5,217,375 | A | * | 6/1993 | Oden et al. .................. 433/218 |
| 5,342,201 | A | * | 8/1994 | Oden .......................... 433/223 |
| 5,614,330 | A | | 3/1997 | Panzera |
| 5,667,548 | A | | 9/1997 | Graule |
| 5,718,749 | A | * | 2/1998 | Horiuchi et al. ......... 106/38.35 |
| 5,775,912 | A | * | 7/1998 | Panzera et al. ............. 433/223 |
| 5,788,891 | A | | 8/1998 | Gauckler |
| 5,849,068 | A | | 12/1998 | Hofmann |
| 5,900,201 | A | | 5/1999 | Chatterjee |
| 5,910,273 | A | * | 6/1999 | Thiel et al. ................... 264/16 |
| 5,948,335 | A | | 9/1999 | Gauckler |

(Continued)

FOREIGN PATENT DOCUMENTS

CH    675120 A5    8/1990

(Continued)

OTHER PUBLICATIONS

Filser, F; Kocher, P.P; Luthy, H.; Scharer, P.; Gauckler, L. All-Ceramic Dental Bridges by the Direct Ceramic Machining Process (DCM), Bioceramics, vol. 10, Oct., 1997.

Primary Examiner—Ralph A. Lewis
(74) Attorney, Agent, or Firm—Buchanan Ingersoll PC

(57) ABSTRACT

Ceramic precursor powders are combined with a binder and pressed into blocks or similar shapes to form green bodies. The ceramic powders consist of fairly uniform particles thoroughly dispersed to be essentially free of agglomerates such that it will sinter predictably and isotropically without appreciable distortion. The green bodies may be soft-sintered to a bisque density less than about eighty five percent of the final density. The soft-sintered blocks are then milled to a desired shape and sintered to a final density rendering a high strength dental restorative material. The material may be aluminum oxide, partially stabilized zirconium oxide, mixtures of the two, mullite or any suitable oxide that may be sintered to high strength (i.e., greater than 250 MPa).

19 Claims, 1 Drawing Sheet

U.S. PATENT DOCUMENTS 5,968,424 A * 10/1999 Shimosawa et al. .......... 264/19
6,063,314 A *  5/2000 Chadwick .................... 264/16
6,133,174 A * 10/2000 Brodkin et al. ................ 501/6
6,136,241 A   10/2000 Gauckler
6,354,836 B1 *  3/2002 Panzera et al. ............. 433/215
6,691,763 B1 *  2/2004 Bond ........................ 164/4.1

FOREIGN PATENT DOCUMENTS

WO     WO 99/47065     9/1999

* cited by examiner

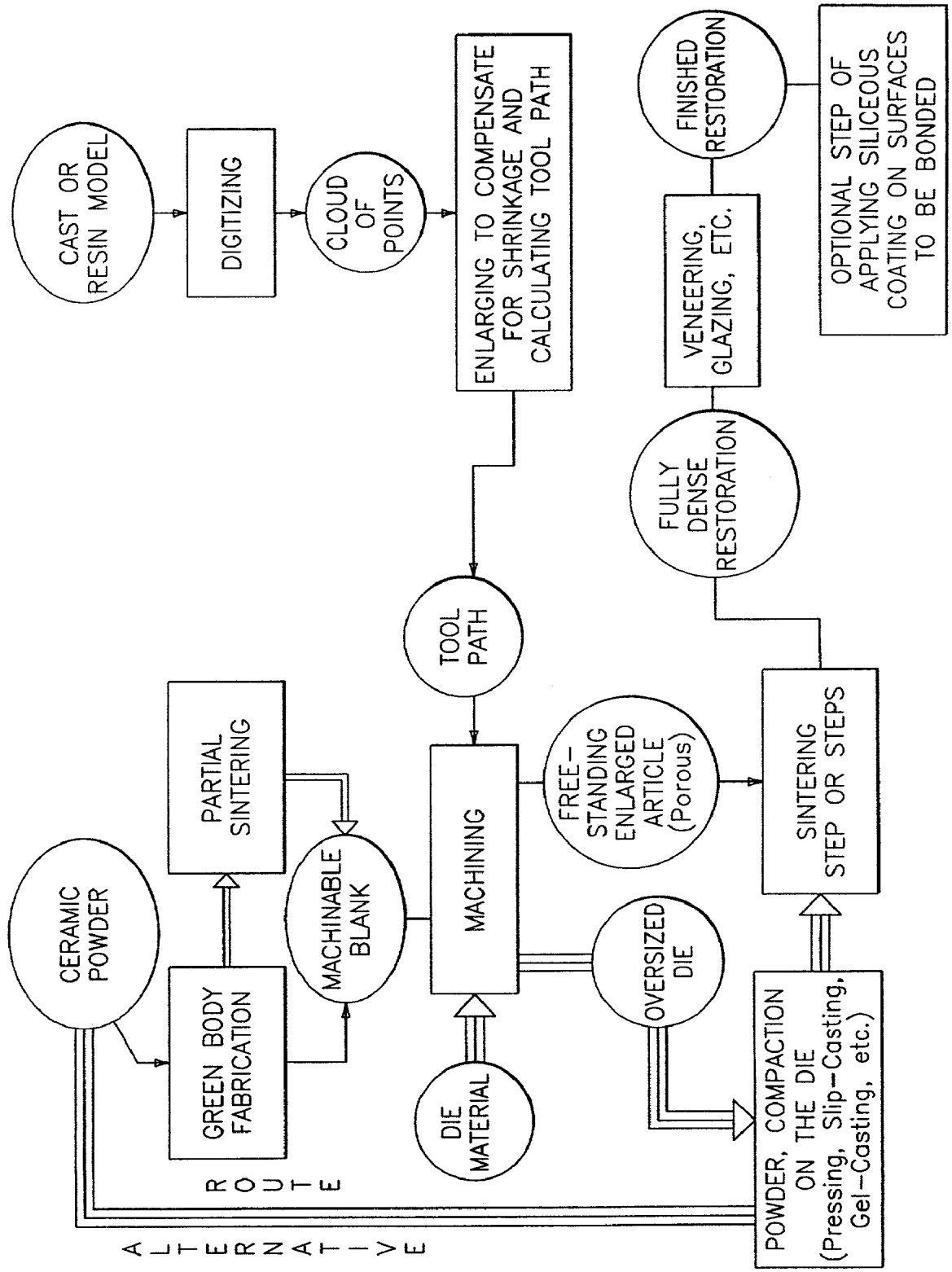

METHODS OF PRODUCING DENTAL RESTORATIONS USING CAD/CAM AND MANUFACTURES THEREOF

CROSS-REFERENCE TO RELATED APPLICATIONS

This application is a division of U.S. application Ser. No. 09/376,921 filed Aug. 18, 1999, now U.S. Pat. No. 6,354,836 which claims priority to Provisional Application No. 60/097,216 filed Aug. 20, 1998, both of which are hereby incorporated by reference.

FIELD OF THE INVENTION

This invention relates to methods of manufacturing all-ceramic dental restorations and more specifically to methods of manufacturing dental restorations using CAD/CAM techniques.

BACKGROUND OF THE INVENTION

The fabrication of current all-ceramic dental restorations often requires extensive labor and time and the proficiency of highly skilled technicians Many state-of-the-art dental restorations reveal a sense of artistry that can typically only be achieved manually or "by hand." While aesthetics are preserved with this process, microstructural inhomogeneities may appear, affecting strength and reliability. The industry has attempted to automate this process by, for example, pressing crowns. Although pressable crowns reduce the time required to produce a crown, about two hours of concerted effort is necessary to complete a crown. Pressed crowns may also suffer from similar strength and relability problems typical of "hand made" crowns.

Computer assisted design/computer assisted milling (CAD/CAM) processes and equipment have been recently introduced into the dental industry. In these processes a three-dimensional image of a stump of a tooth is created along with the teeth surrounding the stump in an effort to create a dental restoration which is to be placed over the stump. This image is displayed on a computer screen. Based on the stump and surrounding teeth, the dental technician may then select a tooth from a plurality of tooth forms stored in the computer to best fit the stump. The selected tooth is projected onto the stump until an optimum positioning and fit of the dental restoration is achieved. The digital data concerning the dental restoration thus formed are supplied to a numerically controlled milling machine operating in three dimensions. The milling machine cuts a blank of metal or porcelain material into the dental restoration design based on the data supplied.

U.S. Pat. No. 4,663,720 to Duret and commonly assigned U.S. Pat. No. 5,775,912 to Panzera et al. each teach CAD/CAM systems and materials which are designed to reduce labor and increase reliability and are herein incorporated by reference. U.S. Pat. No. 5,775,912 is directed to a method of making a dental restoration using soft-sintered porcelain pellets. The method requires the step of investing the tooth structure with an investment refractory material prior to fusing and fully densifying because the glass-ceramic will begin to flow during this step. The investment refractory material provides a mold to maintain the shape of the glass-ceramic during sintering.

U.S. Pat. No. 5,910,273 to Thiel teaches a process for the manufacture of dental materials using CAD/CAM methods wherein a porosity-sintered blank is milled to a desired shape. In order to densify the material, it must be infiltrated with a glass material.

CAD/CAM and copy milling systems designed for the dental industry by Vita Celay, Siemens and Nobelpharma have also been shown to reduce labor. However, some of the materials used in these systems have been shown to be weak or unaesthetic. Moreover, it has been observed, that the use of fully fused dental porcelain pellets wear down cutting and milling tools and significantly slow down the process of dental restoration fabrication. The milling of fully fused dental porcelains may result in excessive chipping and flaking, thus affecting the precision of the milling operation and ultimately the fit between the restoration and the patient's natural teeth.

There is a need to provide materials for use in CAD/CAM operations that are strong and aesthetically pleasing. It is desirable to provide materials for use in CAD/CAM operations that reduce wear of cutting tools on milling machines.

SUMMARY OF THE INVENTION

These and other objects and advantages are accomplished by the material of the present invention comprising a soft-sintered or non-sintered (held together by binders) block of ceramic material. The ceramic material consists of fairly uniform particles thoroughly dispersed to be essentially free of agglomerates such that it will sinter predictably and isotropically without appreciable distortion. The material may be aluminum oxide, partially stabilized zirconium oxide, mullite, any suitable oxide ceramic or glass-ceramic material which may be sintered to high strength (i.e., greater than 250 MPa, and preferably greater than 400 MPa) or mixtures thereof The ceramic materials are used to manufacture dental materials including, but not limited to, orthodontic appliances, bridges, space maintainers, tooth replacement appliances, splints, crowns, partial crowns, dentures, posts, teeth, jackets, inlays, onlays, facings, veneers, facets, implants, abutments, cylinders, and connectors.

In one embodiment of the method of the invention, ceramic powders are combined with a binder and pressed into blocks or similar shapes to form green bodies. The ceramic powders consist of fairly uniform particles thoroughly dispersed to be essentially free of agglomerates such that they will sinter predictably and isotropically without appreciable distortion. The green bodies are milled to a desired shape which is oversized to account for anticipated shrinkage during the sintering stage, and sintered to a final density rendering a high strength dental restorative material. The "plastic state" of the green bodies allows for easy milling into complicated shapes. The material may be aluminum oxide, partially stabilized zirconium oxide, mixtures of the two, mullite or any suitable oxide or glass-ceramic material that may be sintered to high strength (i.e., greater than 250 MPa, and preferably greater than 400 MPa) or mixtures thereof.

In another embodiment of the method of the invention, ceramic precursor powders are combined with a binder and pressed into blocks or similar shapes to form green bodies. The ceramic powders consist of fairly uniform particles thoroughly dispersed to be essentially free of agglomerates such that it will sinter predictably and isotropically without appreciable distortion. The green bodies are soft-sintered to a bisque density that is between about fifty percent (50%) and about eighty-five percent (85%) of the final density. The soft-sintered blocks are then milled to a desired shape, which is oversized to account for anticipated shrinkage during the sintering stage, and sintered to a final density rendering a high strength dental restorative material. The soft-sintered state of the blocks allows for easy milling into complex or elaborate shapes. The material may be aluminum oxide, partially stabilized zirconium oxide, mixtures of the two, mullite or any suitable oxide or glass-ceramic that may be sintered to high strength (i.e., greater than 250 MPa, and preferably greater than 400 MPa) and mixtures thereof.

In yet another embodiment of the method of the invention, a computer assisted milling machine is used to mill a die that is an oversize copy of a patient's tooth or teeth. Thereafter, a ceramic powder with or without binder is applied onto the machined die and the powder-die pair is isostatically pressed to allow the powder to form a uniform mass. Powders can be applied by slip-casting or gel-casting. The amount of die oversized is equivalent to the amount of shrinkage expected for the ceramic powder. The isostatically pressed mass will shrink uniformly when sintered at a sufficiently high temperature to form a dental coping. The die material shrinks considerably more than the coping or melts or burns out and does not interfere with it. The ceramic coping material consists of fairly uniform particles thoroughly dispersed to be essentially free of agglomerates such that it will sinter predictably and isotropically without appreciable distortion. The material may be aluminum oxide, partially stabilized zirconium oxide, mullite or any suitable oxide or glass-ceramic that may be sintered to high strength (i.e., greater than 250 MPa, and preferably greater than 400 MPa), or mixtures thereof.

BRIEF DESCRIPTION OF THE DRAWINGS

Features of the present invention are disclosed in the accompanying drawing, wherein:

FIG. 1 is flow chart showing the various steps involved in the process herein.

DESCRIPTION OF THE INVENTION

The present invention is directed to materials and methods for manufacturing dental restorations. The materials used to manufacture the dental restorations include ceramic materials having a finally sintered strength of greater than about 250 MPa, and preferably greater than 400 MPa. Preferably, the ceramic materials include aluminum oxide, partially stabilized zirconium oxide, mullite, or other oxides or glass-ceramic materials and/or mixtures thereof. The ceramic powders used to manufacture the dental materials consist of fairly uniform particles thoroughly dispersed to be essentially free of agglomerates such that they will sinter predictably and isotropically without appreciable distortion. The particle size may be in the range of about 0.1 to about 100 microns and is preferably in the range of about 1 to about 30 microns.

FIG. 1 provides a flow chart showing the steps involved in the process herein. In one embodiment of a method of manufacturing dental restorations, green bodies are formed using any of the known forming methods including but not limited to pressing, uniaxial or isostatic, extrusion, slip casting, gel casting and injection molding. The preferred choice of the method to consolidate green bodies is cold isostatic pressing (CIP) which is associated with one of the highest degrees of homogeneity attainable in green density. However, uniaxial pressing is equally applicable for pressing certain shapes such as short cylinders. The green bodies are formed into any desired shape and configuration which will render a dental restoration. Fairly uniform, free flowing particles are required for pressing. Binders such as clays, cellulose, polyvinyl alcohol (PVA), polyethylene glycol, wax, TEOS, and the like may be mixed with ceramic powders to retain the shape of the green bodies during and after forming. The invention is in no way limited to the stated binders, and any suitable binder may be used herein to achieve the desired results. The density of the green bodies is from about fifty percent (50%) to about seventy-five percent (75%) percent of theoretical density. In accordance with the process herein, after forming the ceramic powder into green bodies, the bodies may be machined to the shape of a dental material such as a coping, using a computer assisted miller. For purposes of example, a coping will be used to explain the process herein. The shape of the coping is determined from data received by scanning the tooth or die of the tooth to be restored. The size of the coping which is machined is oversized to allow for shrinkage when the coping is sintered. The linear dimensions of the coping are typically about eight percent (8%) to about twenty-five percent (25%) larger than the size of the final coping since the linear shrinkage of the coping after sintering is about eight percent (8%) to about twenty-five percent (25%). The coping is then sintered to full density at time and temperatures appropriate for the material used. There is no need to invest the coping with a refractory material in the method herein because the material will retain its shape during the sintering process independently of any mold or die.

In another embodiment of a method herein, green bodies are formed as described above and soft sintered to provide soft-sintered blocks having bisque densities between about fifty percent (50%) and about eighty-five percent (85%) of the theoretical density. The soft sintering process involves heating pressed or compressed green bodies which have been formed at ambient temperature to a temperature at which only partial sintering occurs to achieve the aforementioned bisque densities. The soft-sintered blocks possess a white, chalky appearance and are somewhat porous. This situation is in contrast to fully sintered processes which produce blocks having a density greater than ninety-five percent of theoretical density and having little or no porosity. Preferably, the soft-sintered blocks are produced by placing a suitable amount of ceramic powders, for example, RC-LS DMB aluminum oxide obtained from Reynolds Metal Company, Bauxite, AR or calcined aluminia A3000FL from Alcoa Industrial Ceramics, Pittsburgh, Pa., in a resin bag, and isostatically pressing in a suitable pressing device, e.g., AIP3-12C cold isostatic pressing device from AIP Inc., Columbus, Ohio, and compressing under pressure, such as, for example, under 50,000 psi into a block at ambient temperature. Thereafter, the block is heated in a furnace, such as for example, a Deltech furnace available from Deltech Inc. to a temperature ranging from about 1225° C. to about 1350° C. to soft-sinter the blocks The resulting soft-sintered blocks possess a density which is less than about eighty-five (85%) percent, typically less than about seventy-five percent (75%) of the theoretical density of the block.

The soft-sintered blocks may then be machined with a computer assisted miller. The shape of the coping is determined from data received by scanning the tooth or die of the tooth to be restored. The size of the coping which is machined is oversized to allow for shrinkage when the coping is sintered. Depending upon the material used, the linear dimensions of the coping may range from a size that is about six percent (6%) to about twenty two percent (22%) larger than the size of the final coping based on the linear shrinkage of the bisque body which may range from about six percent (6%) to about twenty two percent (22%) shrinkage thereof The coping is then sintered to full density at the temperature-time cycle specific for the material used, e.g., for alumina, at about 1600° C. for about four hours. The coping or other dental material may then be coated with various thin layers of pigmented porcelain to provide a finished surface for the dental restoration as described in U.S. Pat. No. 5,614,330 to Panzera which is hereby incorporated by reference.

In yet another embodiment of the present invention, a dental restoration is fabricated using an oversized die of a patient's tooth or teeth. The die may be formed by using a computer assisted miller. The die is oversized in comparison to the actual size of the tooth to account for the amount of shrinkage that will occur to the material being used with the die to fabricate the dental restoration. The ceramic powder is then compacted on this die. The extent of the "oversize" of the die and thus, the coping or restoration being formed therefrom will depend upon the material being used and the relevant shrinkage properties thereof. The material used to fabricate the restoration may include any ceramic, glass-ceramic or oxide material having a strength greater than about 250 MPa, and preferably greater than about 400 MPa. Preferably, the ceramic materials include aluminum oxide, partially stabilized zirconium oxide, mullite, or mixtures thereof.

The die may be fabricated of a porous or nonporous material depending upon the forming process of the restoration. The fabrication process for the restoration may include but is not limited to slip casting, pressing, isostatic pressing, extrusion, injection molding and gel casting. If, for instance, slip casting is employed, the mold is typically fabricated of gypsum or a porous plastic material in order that water may be extracted from the slip by the mold. Other processes, such as gel casting, do not require a porous mold to remove liquid.

Depending upon the process used herein, such as for example, isostatic pressing, the die may be partially sintered such that it will have sufficient compressive strength to withstand the forces exerted on it during pressing or sintering. High temperature casting investment materials include commercially available materials such as Ceramacast™ investment materials from Aremco Products Inc., Valley Cottage, N.Y.

In this method, the coping or restoration formed may be removed from the die prior to sintering. Sintering may involve one step whereby the die is removed prior thereto, or sintering may involve two steps whereby the die is removed after the first sintering step and before the high temperature, second sintering step. Removal of the die is not a critical step of the processs and proper selection of the technique depends on the ceramic powder and sintering temperatures used. Slip-casting is one of the preferred techniques for compaction of powder on a die since equipment is already commercially available for automation of the slip-casting operation whereby mass-production of restorations is possible.

Alternatively, the die may be fabricated of a material that shrinks away from the dental restoration or coping during sintering. As yet another option, the die may be formed of a material that disappears, for example, by melting, thermal decomposition and/or burn-out. A refractory die material can contain particles of compounds with near zero or negative thermal expansion such as, $NaZr_2P_3O_{12}$ (NZP) and $ZrW_2TO_7$ to assure proper shrinkage thereof. Other particulate ceramics that are frequently used as ceramic filler for the die material are quartz, cristobolite, fused silica or colloidal silica.

The die used herein is oversized in an amount based on the amount of shrinkage which will occur in the powder which is used to form the restoration. As set forth herein, ceramic or glass-ceramic powders are used to form the dental restoration and the shrinkage varies from material to material. Preferably, high strength ceramic or glass-ceramic materials are used, such as alumina, zirconia, or mullite and will shrink upon sintering in the range of about fifty percent (50%) to about twenty five percent (25%) of the initial volume of the dental restoration to be formed or about eight percent (8%) to about twenty five percent (25%) of the initial length of the dental restoration to be formed. The "oversize" of the die is thus based on that amount of shrinkage. The following formula is used to calculate volume shrinkage whereby $V_F$ is the final volume and $V_O$ is the original volume.

$$\left(\frac{V_O - V_F}{V_O}\right) \times 100\% = \text{Volume Shrinkage}$$

The ceramic coping or restoration material consists of fairly uniform particles thoroughly dispersed to be essentially free of agglomerates such that it will sinter predictably and isotropically without appreciable distortion. The coping may then be coated with various thin layers of pigmented porcelain to form the surface of a dental restoration.

Dental articles should be sintered in the homogeneous temperature zone of the furnace where the temperature gradients are practically absent. Accordingly, during the partial or soft sintering of the green bodies and further during the final or full sintering of the milled or pressed bodies, no thermal gradients are present in the furnace to further prevent distortion and uneven shrinkage in the finally sintered body. The following examples illustrate the practice of the invention.

EXAMPLE 1

Green bodies of four commercially available materials were cut from large uniaxially pressed plates of one inch in thickness into blocks having dimensions of 1.0×0.6×0.6 in³. The four materials were (1) AD-995 Alumina (99.5% alumina); (2) FG-985 Alumina (a finer particle size alumina); (3) ZTA Zirconia (zirconia toughened alumina); and (4) YTZP Zirconia (four mole percent yttria stabilized tetragonal zirconia polycrystal). All four materials were supplied by Coors Ceramic Company, Golden, Colo. The blocks were obtained from the supplier in the soft-sintered state. The supplier soft-sintered the blocks using production kilns at various undisclosed firing cycles designated below in Table 1. The soft sintered blocks were characterized by bisque densities ranging from about fifty percent (50%) to about eighty four percent (84%) of theoretical density and corresponding bisque-to-final linear shrinkages and linear shrinkages are tabulated below. Bisque density is equal to a percentage of the final density. Linear shrinkage is equal to 100% multiplied by one or more dimensions of the soft sintered block minus one or more of the same dimensions of the fully/final sintered block. That value is then divided by the one or more dimensions of the soft sintered block.

Bisque Density=% Final Density

Linear Shrinkage=100%×($L_{soft\ sintered}-L_{final\ sintered}$)/$L_{soft\ sintered}$ where L is one or more dimensions of the block of material Bisque Density is shown in parentheses in Table 1.

Linear Shrinkage is shown next to the Bisque Density outside the parentheses in Table 1.

TABLE 1

| BISQUE FIRING CYCLE OF MATERIAL | I3 FIRING CYCLE (Bisque Density) Linear Shrinkage | I2 HI FIRE FIRING CYCLE (Bisque Density) Linear Shrinkage | I2 LOW FIRE FIRING CYCLE (Bisque Density) Linear Shrinkage | PARAGON FIRING CYCLE (Bisque Density) Linear Shrinkage |
|---|---|---|---|---|
| ZTA | (84.1) 5.61 | (64.1) 13.78 | (61.2) 15.09 | (60.7) 15.35 |
| YTZP | fully dense | (76.9) 8.37 | (50.2) 20.52 | (49.3) 21.00 |
| FG-985 | (73.8) 9.62 | (63.2) 13.65 | (63.9) 13.87 | (63.2) 14.19 |
| AD-995 | (74.4) 9.41 | (62.5) 14.51 | (60.5) 15.46 | (60.3) 15.51 |

The soft-sintered blocks were machined using a CAD/CAM device manufactured by CAD/CAM Ventures, Irving, Tex. The device includes a contact digitizer and a machining unit equipped with carbide tools and utilizes dry milling. Thin-walled boxes having dimensions of about 8.6×8.2×8.2 mm$^3$ were milled from the blocks to evaluate machinability. The thin-walled boxes were sintered to full density and evaluated for final shape and for linear shrinkage along three axes. Their rectangular shape was perfectly maintained and shrinkage was found to be nearly isotropic with an absolute difference of shrinkage along the three axes not exceeding about 1%. Based on the amount and manner of shrinkage, the method of the invention was applicable on all four materials.

EXAMPLE 2

The same four materials used in Example 1 were used in this example. The soft-sintered blocks were machined into copings using a CAD/CAM file from a previously digitized model. The quality of margins, integrity of edges and ability to withstand handling were evaluated for various bisque densities. The linear shrinkages corresponding to the workable bisque densities for two of the alumina samples and ZTA were established to be in the range of about 10% to about 13%. Materials with linear shrinkage of less than about 9% were found not to be machinable by the dry process with carbide tools. Materials with linear shrinkages of more than about 13% with the exception of TZP were found to be too weak to maintain integrity of edges and withstand handling. Consequently, the linear shrinkages corresponding to the workable bisque densities for two alumina materials and ZTA were established in the range of 10% to 13%. Bisque density is important both to assure optimal machinability and tighter tolerances on final dimensions. It was found essential to assure homogeneity of density in the green body as well as homogeneity of temperature distribution in the sintering furnace to limit temperature gradients in the furnace to less than ±10° C. and preferably less than ±5° C. Considering that the specimens were prepared by the manufacturer as described above without specific care for homogeneity of green bodies, the method of this invention was deemed to be applicable to all four evaluated materials. The preferred choice of the method to consolidate green bodies is cold isostatic pressing which is associated with one of the highest attainable homogeneities of green density However, uniaxial compaction can be used for certain shapes such as short cylinders. Other techniques may be slip casting, gel casting, extrusion and injection molding.

EXAMPLE 3

Two of the above evaluated materials, AD-995 and FG-985 were supplied by Coors Ceramics Company (Golden, Colo.) as pre-sintered cylinders having dimensions of about 1.128" in diameter and about 0.75" in height. The cylinders were presintered (bisque sintered) at the temperatures listed in Table 2. Corresponding bisque-to-final linear shrinkages at the respective bisque sintering temperatures are likewise set forth in Table 2 below.

TABLE 2

| BISQUE SINTERING TEMPERATURE ° C. | FG-985 LINEAR SHRINKAGE | AD-995 LINEAR SHRINKAGE |
|---|---|---|
| 1225 | 12.87 | 13.30 |
| 1250 | 12.57 | 12.81 |
| 1275 | 11.87 | 12.14 |
| 1300 | 11.37 | 11.57 |
| 1325 | 10.60 | 10.85 |
| 1350 | 9.90 | 9.93 |

Using a CAD/CAM device and digitizer manufactured by CAD/CAM Ventures, Irving, Tex., the model of the tooth preparation was digitized and the obtained cloud of points was enlarged proportional to the linear shrinkage data set forth in Table 2 to compensate for bisque-to-final sintering shrinkage. The copings were milled from the blocks according to the resulting CAD file. The copings were sintered to full density at the following temperature cycle: ramp 5° C./min to 1000° C., 2° C./min ramp to 1600° C., soak at 1600° C. for four hours. The fully sintered copings were fitted onto the original model and their fit was evaluated by an experienced dental technician as adequate.

EXAMPLE 4

A plaster block was made from plaster die powder and mixing liquid manufactured by Vita Zahnfabrick, Bas Sackingen, Germany. Using the same file and the same CAD/CAM machine as in the previous example, an oversized die was machined from the block of plaster. Aqueous slips were prepared with fifty-five volume percent (55%) alpha-alumina A3000FL, available from Alcoa, Pittsburgh, Pa., citric acid (0.1 wt % dry weight basis alumina), and distilled water. For best results, slip pH was adjusted between 6.8 and 10.9 with tetramethylammonium hydroxide. The slip was then ball-milled with alumina grinding media for five hours. The slip was applied on the die by brush and dried for 24 hours at room temperature. Sintering was carried out in two steps in a Deltech furnace (DT-31-SBL-9912) from Deltech Inc., Denver, Colo. After sintering at 1100° C. for 2 hours, the plaster die was removed and a free-standing coping was placed on a piece of alumina paper (APA-3) from Zicar Products Inc., Florida, N.Y. and sintered to full density at 1600° C. for four hours. The fully sintered copings were fitted on the original model and their fit was evaluated by an experienced dental technician as adequate.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of manufacturing a dental restoration comprising:
    fabricating a die for the dental restoration, wherein the die is oversized and wherein the die is partially sintered prior to application of the powder thereon;
    applying powder selected from ceramic, glass ceramic powder and mixtures thereof onto the die in the shape of the dental restoration;
    sintering the powder to form the dental restoration.

2. The method of claim 1 wherein the die is oversized in an amount to account for proper shrinkage of the powder after sintering.

3. The method of claim 1 wherein fabricating the die comprises machining the die from a block of material.

4. The method of claim 3 wherein the machined die is machined from data taken from a patient's mouth.

5. The method of claim 3 wherein the machined die is machined from data taken from an impression of a patient's mouth.

6. The method of claim 1 wherein the die is removed from the shaped powder prior to sintering.

7. The method of claim 1 wherein the dental material is sintered in the range of about 1400 to about 1500° C. for a time ranging from about one to about four hours.

8. The method of claim 1 wherein the ceramic powder linearly shrinks isotropically about 8 to about 25% during sintering.

9. The method of claim 1 wherein the powder comprises a material that may be sintered to a strength of greater than about 250 MPa.

10. The method of claim 1 wherein the powder comprises aluminum oxide, partially stabilized zirconium oxide, mullite, or mixtures thereof.

11. The method of claim 1 wherein the die is fabricated of a porous material.

12. The method of claim 11 wherein the porous material comprises gypsum.

13. The method of claim 1 wherein applying the powder comprises pressing, extrusion, slip casting, gel casting or injection molding.

14. The method of claim 13 wherein the dental restoration is pressed at 50,000 psi at about ambient temperature.

15. The method of claim 1 wherein one or more binders is mixed with the powder prior to application to the die.

16. The method of claim 1 wherein the powder is of uniform particle size.

17. The method of claim 16 wherein the particle size is in the range between about 1 and about 3 microns.

18. The method of claim 1 wherein the dental restoration is an orthodontic appliance, bridge, space maintainer, tooth replacement appliance, splint, crown, partial crown, denture, post, tooth, jacket, inlay, onlay, facing, veneer, facet, implant, abutment, cylinder, or connector.

19. The method of claim 1 wherein the powder is substantially homogeneous.

* * * * *